United States Patent
Bae et al.

(10) Patent No.: US 6,326,178 B1
(45) Date of Patent: Dec. 4, 2001

(54) METHOD FOR SYNTHESIZING A COMPOSITE OF A CONDUCTIVE MACROMOLECULE AND A PROTEIN

(75) Inventors: Yon-Han Bae; Won-Jun Sung, both of Kwangju (KR)

(73) Assignee: Kwangju Institute of Science and Technology, Kwangju (KR)

( * ) Notice: Subject to any disclaimer, the term of this patent is extended or adjusted under 35 U.S.C. 154(b) by 0 days.

(21) Appl. No.: 09/478,742

(22) Filed: Jan. 6, 2000

(51) Int. Cl.$^7$ .................................................. C12N 11/08
(52) U.S. Cl. ........................ 435/180; 435/190; 435/182; 435/287.9
(58) Field of Search ................................... 435/180, 182, 435/287.9, 190

(56) References Cited

U.S. PATENT DOCUMENTS 4,246,351 * 1/1981 Miyake et al. ...................... 435/182

FOREIGN PATENT DOCUMENTS

0595800-B1 * 10/1996 (EP) .

OTHER PUBLICATIONS

"Electrochemical Polymerization of Pyrrole", Diaz Et Al., Journal of Chemical Society and Chemical Communication, pp. 635–636 (1979).

"Conducting Polymers Derived from Pyrrole", Street Et Al., Solid State Science 49, Organic Molecular Aggregates, Springer–Verlag, New York (1983).

"Charge–Controllable Polypyrrole/Polyelectrolyte Composite Membranes: Part II Effect of Incorporated Anion Size on the Electrochemical Oxidation–Reduction Process", Shimidzu Et Al., Journal of Electroanalytical Chemistry 224, (1987), pp. 123–135.

"Poly(N–Methylpyrrolylium) Poly(Styrenesulfonate). A Conductive, Electronically Switchable Cation Exchanger that Cathodically Binds and Anodically Releases Dopamine", Miller Et Al., Macromolecules 1987, 20, 1594–1597.

* cited by examiner

Primary Examiner—Christopher R. Tate
Assistant Examiner—Kailash C. Srivastava
(74) Attorney, Agent, or Firm—Sheridan Ross, P.C.

(57) ABSTRACT

Disclosed herein is a method for synthesizing a composite of a conductive macromolecule and a protein component. The method utilizes, as the protein component, a protein composite consisting of protein bonded to a macromolecular anion. The protein composite can serve as a dopant to improve an electrical conductivity of the conductive macromolecule and also to impart multifunctional properties to the conductive macromolecule.

4 Claims, 1 Drawing Sheet

METHOD FOR SYNTHESIZING A COMPOSITE OF A CONDUCTIVE MACROMOLECULE AND A PROTEIN

BACKGROUND OF THE INVENTION

1. Field of the Invention

The present invention relates to a method for synthesizing a composite of a conductive macromolecule and a protein component, in which a protein composite consisting of protein bonded to a macromolecular anion is used as the protein component.

2. Description of the Prior Art

A conductive macromolecule is a material on which a great interest is focused, at present day, due to its excellent physical properties inherent in a macromolecule. Such a conductive macromolecule is widely used in a variety of application fields, such as, for example, the preparation of a conductive plastic for preventing static electricity, the separation of compounds, a compound sensor, the delivery of a drug, a bio sensor, a diagnosis device, etc. Since being successively synthesized using a monomolecular anion as an additive, (see, Journal of chemical society and chemical communication 635 (1979)), this conductive macromolecule has been continually studied to achieve an improvement in the electrically conductive property and mechanical property. In order to improve the performance of its conductive macromolecule, although there was carried out a study on the chemical modification of the conductive macromolecule (see, Solid State Science 49 (1983)), this study did not provide a satisfactory result. In addition, even if an additive, such as a macromolecule anion, was used to adjust the physical property of the conductive macromolecular (see, Journal of Electroanalytical chemistry 224, 123 (1987), and Macromolecules 20, 1594 (1987)), it is disadvantageous in that the additive is limited in use to commercially produced macromolecules or a neutral macromolecule. Methods used up to now to synthesise a composite of the conductive macromolecule and a protein, include a method in which protein itself is used as an additive to the conductive macromolecule, and a method in which protein is composed with a monomer of the conductive macromolecule and the resulting composite is electrically polymerized. Such methods, however, have various problems, such as the limitation on usable kinds of protein, an insufficient efficiency on the synthesis of the conductive macromolecule-protein composite, the elution of protein into the conductive macromolecule-protein composite, etc.

SUMMARY OF THE INVENTION

It is therefore an object of the present invention to solve the above-mentioned problems, and to provide a method for synthesizing a composite of a conductive macromolecule and a protein component, in which a protein composite consisting of protein bonded to a macromolecular anion is used as the protein component (dopant), thereby improving the electrical conductivity of the conductive macromolecule, and imparting multifunctional properties to the conductive macromolecule.

BRIEF DESCRIPTION OF THE DRAWINGS

Other objects and aspects of the invention will be apparent from the following description of embodiments with reference to the accompanying drawing, in which.

DETAILED DESCRIPTION OF THE PREFERRED EMBODIMENTS

Figure 1:
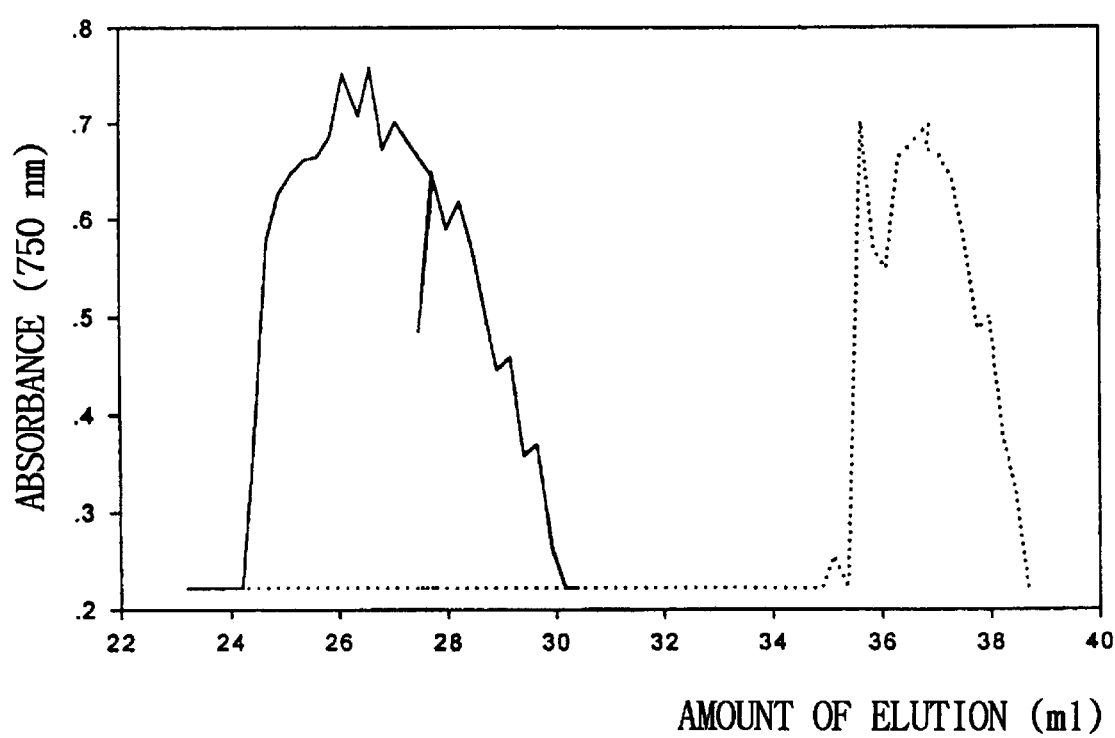
FIG. 1 shows gel filtration chromatograms of a protein composite and glucose oxidase, in which a gel filtration chromatogram of the protein composite is indicated in a full line, and a gel filtration chromatogram is indicated in a dot line.

The foregoing and other objects, features and advantages of the invention will be apparent to those skilled in the art to which the present invention relates from reading the following specification.

As an additive to a conductive macromolecule must have a negative charge to neutralize a positive charge generated during the electrical polymerization of the conductive macromolecule, protein useful as the additive to the conductive macromolecule is limited in use depending on its surface charge state. The surface charge of a protein molecule is dependent on amino acids constituting the molecule, and carboxylate (—COO$^-$) mainly serves as a functional group forming a negative charge. Since such a functional group has a pKa value ranging from pH 4 to 5, it is sensitively changed in the quantity of charge depending on pH, particularly at low pH range. When electrically polymerizing the conductive macromolecule, a redox reaction may result in a decrease in a pH of a solution containing the conductive macromolecule and the additive. This acts as a limiting factor in the synthesis of an electrically conductive composite containing the protein. On the other hand, where the protein is pH 7 or more, it can not be used as the additive to the conductive macromolecule. Consequently, any protein can result in the synthesis of a more effective and stable protein-conductive macromolecule composite which can be enlarged in the application field, as long as it may be used for the synthesis of the conductive macromolecule without being influenced by a change in the pH of the solution containing the conductive macromolecule and the protein.

In accordance with an embodiment of the present invention, a protein composite useful as a protein component in the synthesis of a composite of a conductive macromolecule and the protein component is prepared by bonding glucose oxidase to a macromolecular anion having a sulfonate group (—SO$_3^-$). Because the macromolecular anion has the sulfonate group as a strong acid group of a pKa value ranging from 1 to 2, it is not influenced by a change in the pH of a solution containing the conductive macromolecule and the protein component when synthesizing the composite of the conductive macromolecule and the protein component. In other words, as a material chemically bonded to such a macromolecular anion can be used as a dopant in the synthesis of the conductive macromolecule regardless of its charge state, it enables any of proteins to be effectively formed into a composite with the conductive macromolecule.

Moreover, the macromolecule anion used in the practice of the present invention is preferably polyethyleneglycol monoacrylate having a molecular weight in the range of 1,000 to 10,000. And, protein used in the practice of the present invention is glucose oxidase.

As used herein, the term "protein component" is used to substantially mean protein and to distinguish "protein" from the term "protein composite".

The present invention will now be described in detail with reference to the following examples. However, these examples are presented for better understanding of the present invention only, and are not intended to limit the scope of this invention in any way.

EXAMPLE 1

Carboxylation of Polyethylene Glycol Monoacrylate at its End Group.

50 g of polyethyleneglycol monoacrylate is dissolved in 300 ml of methylene chloride to remove impurities. Then, the resulting polyethyleneglycol monoacrylate is precipitated in diethyl ether. A purified polyethyleneglycol monoacrylate has a double bond and a hydroxy group at its both ends, respectively. Among these end groups, the hydroxy group is substituted with an amine group and a highly reactive carboxylic group as follows.

50 g (33.3 mmole) of a purified polyethylene glycol monoacrylate is charged into a reactor, dissolved at a temperature of 40° C. to 45° C. under a vacuum, and then dried at room temperature under a vacuum for 24 hours to remove moisture. After the dried polyethylene glycol monoacrylate, 5 g (50 mmole) of succinic anhydride, 5.56 g (40 mmole) of triethyl amine, and 4.9 g (40 mmole) of dimethylaminopyridine are dissolved in 450 ml of a purified dioxane, the resulting mixture is left to react at room temperature under atmospheric pressure for 24 hours. After that, dioxine is evaporated out using an evaporator and the resulting reaction mixture is then dissolved in carbon tetrachloride to filter out succinic anhydride that is insoluble in carbon tetrachloride. Next, the filtrate is precipitated in diethyl ether and dried, thereby obtaining polyethylene glycol monoacrylate having an end group substituted with a carboxylic group. Results analyzed for such a product are as follows:

$^1$H-NMR (200 MHz, $D_2O$); $\delta 2.4(COCH_2CH_2COOH)$, $\delta 3.5(OCH_2CH_2)$, $\delta 4.1(OCH_2CH_2OCO)$, ET-IR, 1732 $cm^{-1}$ (C=O), $1664^{-1}$ (C≡N$^+$), 1115 $cm^{-1}$ ($CH_2OCH_2$), 1559 $cm^{-1}$ ($COO^{-1}$).

EXAMPLE 2

Formation of a Copolymer of a Macromolecular Anion (2-acrylamido-2-methylpropanesulfonic acid) and Polyethyleneglycol Monoacrylate Substituted with a Carboxylic Group at an End Group.

2-Acrylamido-2-methylpropanesulfonic acid and polyethylene glycol monoacrylate substituted with a carboxylic group at an end group in the weight ratio of 98 to 2 are dissolved in dimethylsulfoxide at a concentration of 10 wt/vol %. Then, the resulting solution is stirred at room temperature under a vacuum for one hour while degassing. Next, 0.3 mole% of 2,2'-azobisisobutyronitrile or benzoylperoxide as an initiator is added, the resulting mixture is polymerized at a temperature of 60° C. under atmospheric pressure for 24 hours where 2,2'-azobisisobutyronitrile is used as the initiator, or at a temperature of 70° C. under atmospheric pressure for 24 hours where benzoylperoxide is used as the initiator. After the polymerization, dimethylsulfoxide used as a solvent is evaporated out under a vacuum using an evaporator. Thereafter, the resulting mixture is precipitated in diethyl ether to remove an unreacted portion of polyethylene glycol monoacrylate. Next, the resulting material is dried under a vacuum for 24 hours and is then dialyzed for 4 days using a molecular cut off (MWCO) 15,000 Spectra 7 membrane to remove an unreacted portion of 2-acrylamido-2-methylpropanesulfonic acid and an oligomer having a lower molecular weight. Then, the dialyzed material is freeze-dried to obtain the desired copolymer. Results analyzed for the obtained copolymer are as follows:

$^1$H-NMR (200MHz, $D_2O$), $\delta$ 1.38 ($CCH_3CH_3$), $\delta$ 3.5 ($OCH_2CH_2$), FT-IR, 1732 $cm^{-1}$ (C=O), 1650 $cm^{-1}$ (COHN), 1458 $cm^{-1}$ ($CH_3$).

EXAMPLE 3

Synthesis of a Composite Consisting of Glucose Oxidase and Copolymer of a Macromolecular Anion with a Polyethyleneglycol Monoacrylate Substituted with a Carboxylic Acid at an End Group.

(1) Activation of a carboxylic acid in a copolymer containing a macromolecular anion.

In order to allow the reaction of a carboxylic group in a macromolecular anion-containing copolymer with an amine group in glucose oxidase to be taken place in a fast and easy manner, the carboxylic group is activated by a carbodiimide catalyst. Firstly, to prevent the activation of sulfonic acid in the copolymer, sodium hydroxide is added to the copolymer in the amount equal to that of sulfonic acid to convert the copolymer into a form of sodium salt. Then, after the resulting copolymer is dissolved in dimethylsulfoxide at a temperature of 70° C., 1.2 mmole of N-hydroxysuccinic imide and 1.2 mmole of dicyclohexylcarbodiimide are added to the copolymer and the resulting mixture is left to react at a temperature of 70° C. for 24 hours. Next, dicyclohexylurea resulting from the reaction is filtered out. After that, the resulting product is precipitated in diethyl ether, filtered, and then dried for 24 hours.

(2) Synthesis of a composite consisting of a macromolecular anion-containing copolymer and glucose oxidase.

0.11 g of a copolymer, in which a carboxylic group is activated and a macromolecular anion is contained, and 0.5 g of glucose oxidase are dissolved in three phosphate buffer solutions (PBS, pH 5, 6 and 7, 0.1 M concentration), respectively. The resulting three solutions are stirred at a temperature of 4° C. to prevent the modification of glucose oxidase and then left to react for 24 hours. The resultant materials are subjected to an ultra filtration (MWCO 300, 000) to remove unreacted material and then freeze-dried, thereby obtaining the desired composites.

TEST EXAMPLE 1

Identification of a Composite Consisting of a Macromolecular Anion-containing Copolymer and Glucose Oxidase, and Measurement for the Amount of Glucose Oxidase.

The composite of a macromolecular anion-containing copolymer and glucose oxidase was identified from a gel filtration chromatogram of a sample consisting of oxidase glucose bonded to the macromolecular anion, as compared with a gel filtration chromatogram of glucose oxidase, as shown in FIG. 1. In FIG. 1, a full line indicates the gel filtration chromatogram of a sample consisting of glucose oxidase bonded to the macromolecular anion, and a dot line indicates the gel filtration chromatogram of glucose oxidase.

The amount of glucose oxidase in the composite of the macromolecular anion-containing copolymer and glucose oxidase was measured according to the following Lowry method (see, Journal of Biological Chemistry 193, 267 (1951)): Glucose oxidase (peptide bond)+$Cu^{2+}$ →tetradentate-$Cu^{1+}$composite→the introduction of a Lowry agent commercially available under the trade name "Folin & Ciocalter's phenol" from Pierce Co.→a bluish composite→the measurement of transmittancy at 750 nm→the calculation of the glucose concentration.

Results measured for the amount of glucose oxidase in the composite are listed in Table 1 below.

TABLE 1

| Amount of glucose oxidase (GOD) in the composite | | |
|---|---|---|
| pH of the buffer solution in Example 3 | GOD content($\mu$g/ml) | Yield of composite (%) |
| 5 | 750 | 94 |
| 6 | 890 | 109 |
| 7 | 800 | 100 |

TEST EXAMPLE 2

Measurement for Physiological Activity of Glucose Oxidase in a Composite Consisting of a Macromolecule Anion-containing Copolymer and Glucose Oxidase.

A physiological activity of glucose oxidase in a composite consisting of a macromolecule anion-containing copolymer and glucose oxidase was measured in accordance with a Kelly & Reddy test method (see, Journal of Biological Chemistry 265, 3793(1990)). In measuring the physiological activity, 0.2 mmole of o-dianicidine, 20 µg of horseradish peroxidase, and 9.5 mmol of glucose were dissolved in 2 ml of a buffer solution (PBS, pH 7), and the resulting solution was used as a substrate for glucose oxidase. Horseradish peroxidase was started to react with glucose oxidase in a sample as glucose oxidase was added. Then, horseradish peroxidase and glucose oxidase were then incubated at room temperature for 20 minutes. The reaction of horseradish peroxidase and glucose oxidase was terminated by addition of 0.2 ml of 4N aqueous sulfuric acid solution. The physiological activity of glucose oxidase in the sample was obtained by measuring an absorbance at 400 nm, and calculated in terms of a relative physiological activity to a non-polymerized sample. Table 2 below shows the physiological activity of glucose oxidase for each sample.

TABLE 2

Physiological activity of glucose oxidase (GOD) in the composite

| pH of a buffer solution in Example 3 | Relative physiological activity |
|---|---|
| 5 | 136% |
| 6 | 107% |
| 7 | 99% |

As apparent from the above description, the present invention provides a method for synthesizing a composite of a conductive macromolecular and a protein component, using, as the protein component, a protein composite consisting of protein (glucose oxidase) bonded to a macromolecular anion (2-acrylamido-2-methylpropanesulfonic acid). Such a protein composite maintains the physiological activity of glucose oxidase therein at 90% or more without being influenced by the pH of the used solvent, as indicated in Table 2 above. Therefore, the protein composite can serve as a dopant for the highly conductive macromolecule.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A method for synthesizing a composite comprising a conductive macromolecule and a protein component, comprising forming a copolymer of a macromolecular anion by polymerizing a macromolecular anion having a sulfonate group and polyethylene glycol monoacrylate substituted with a carboxylic group at an end group; and reacting the copolymer of macromolecular anion with an amine group of a protein.

2. A method, as set forth in claim 1, wherein said macromolecular anion has a molecular weight in the range of from about 1,000 to about 10,000.

3. A method, as set forth in claim 1, wherein said protein comprises glucose oxidase.

4. A method for synthesizing a composite of a conductive macromolecule and a protein component, comprising:

a. dissolving polyethyleneglycolmonoacrylate in methylene chloride to remove impurities;

b. precipitating said polyethyleneglycolmonoacrylate in diethel ether to form a purified polyethyleneglycolmonoacrylate having a double bond and a hydroxy group;

c. substituting said hydroxy group with an amine group and a carboxylic group;

d. forming a copolymer between a macromolecular ion comprising 2-acrylamido-2-methylpropanesulfonic acid and polyetheneglycolmonoacrylate having a carboxylic group associated therewith;

e. removing any portion of polyethyleneglycolmonoacrylate that has not reacted with said macromolecular anion; and f. forming a composite consisting of glucose oxidase and a copolymer of a macromolecular anion comprising polyethyleneglycomonoacrylate, having a carboxylic acid associated therewith, by allowing, in the presence of a carbodiiamide catalyst, a reaction to occur between said carboxylic group of said macromolecular anion and an amine group associated with said glucose oxidase.

* * * * *

UNITED STATES PATENT AND TRADEMARK OFFICE
CERTIFICATE OF CORRECTION

PATENT NO. : 6,326,178 B1
DATED : December 4, 2001
INVENTOR(S) : Bae, You-Han

It is certified that error appears in the above-identified patent and that said Letters Patent is hereby corrected as shown below:

<u>Title page,</u>
Item [73], should read:

-- [73] Assignee: Kwangju Institute of Science and Technology, Kwangju (KR)

Sooil Development Co., Ltd.
        Seoul (KR) --

Signed and Sealed this

Eleventh Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,326,178 B1
DATED          : December 4, 2001
INVENTOR(S)    : Bae et al.

It is certified that error appears in the above-identified patent and that said Letters Patent is hereby corrected as shown below:

<u>Title page,</u>
Item [73], Assignee, please add:

-- Sooil Development Co., Ltd. of Seoul (KR) --.

Signed and Sealed this

Twenty-fifth Day of March, 2003

JAMES E. ROGAN
*Director of the United States Patent and Trademark Office*